United States Patent
Butler et al.

(10) Patent No.: US 9,408,977 B2
(45) Date of Patent: Aug. 9, 2016

(54) DRIVE MECHANISM FOR A DRUG DELIVERY DEVICE AND DRUG DELIVERY DEVICE

(75) Inventors: Stephen David Butler, Essington (GB); Mark Philip Horlock, Timperley (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 864 days.

(21) Appl. No.: 13/701,943

(22) PCT Filed: Jun. 9, 2011

(86) PCT No.: PCT/EP2011/059562
§ 371 (c)(1),
(2), (4) Date: Apr. 8, 2013

(87) PCT Pub. No.: WO2011/154479
PCT Pub. Date: Dec. 15, 2011

(65) Prior Publication Data
US 2013/0204204 A1    Aug. 8, 2013

(30) Foreign Application Priority Data

Jun. 11, 2010    (EP) .................................... 10165635

(51) Int. Cl.
*A61M 5/315* (2006.01)
*F16H 25/12* (2006.01)

(52) U.S. Cl.
CPC ......... *A61M 5/31528* (2013.01); *A61M 5/3155* (2013.01); *A61M 5/31535* (2013.01);
(Continued)

(58) Field of Classification Search
CPC ..................... A61M 5/31551; A61M 5/31535; A61M 5/3155; A61M 5/31528; A61M 5/31555; A61M 5/31583; A61M 5/31585; A61M 5/31593; A61M 5/31548

USPC .................................................. 604/207–211
See application file for complete search history.

(56) References Cited

U.S. PATENT DOCUMENTS

| 5,308,340 A | 5/1994 | Harris |
| 5,827,232 A | 10/1998 | Chanoch et al. |

(Continued)

FOREIGN PATENT DOCUMENTS

| EP | 1923085 | 5/2008 |
| WO | 99/38554 | 8/1999 |

(Continued)

OTHER PUBLICATIONS

International Search Report for Int. App. No. PCT/EP2011/059562, completed Aug. 29, 2011.

*Primary Examiner* — Nathan R Price
*Assistant Examiner* — Anh Bui
(74) *Attorney, Agent, or Firm* — McDonnell Boehnen Hulbert & Berghoff LLP

(57) ABSTRACT

The drive mechanism comprises a drive member inside a housing, a rotation member and a dose member. The drive member is rotatable with respect to the housing. The rotation member is also rotatable and unidirectionally rotationally engaged with the drive member. The dose member is able to move along a set/deliver path between a first axial position and a second axial position in either direction or to move along a cancel path from the second axial position to the first axial position. An engagement of the dose member with the rotation member causes the rotation member to rotate when the dose member is moved along the set/deliver path. The drive member is not rotated when the dose member is moved along the cancel path. A button in/out spline can be provided for the set/deliver path and a cancel spline for the cancel path.

17 Claims, 11 Drawing Sheets

(52) U.S. Cl.
CPC ....... *A61M5/31548* (2013.01); *A61M 5/31551* (2013.01); *A61M 5/31555* (2013.01); *A61M 5/31583* (2013.01); *A61M 5/31585* (2013.01); *A61M 5/31593* (2013.01); *F16H 25/12* (2013.01); *Y10T 74/18576* (2015.01)

(56) References Cited

U.S. PATENT DOCUMENTS

2005/0055011 A1* 3/2005 Enggaard ............... A61M 5/20 604/500

2006/0153693 A1 7/2006 Fiechter et al.
2010/0036320 A1* 2/2010 Cox ................. A61M 5/31593 604/135
2011/0034902 A1* 2/2011 Markussen ......... A61M 5/3156 604/506

FOREIGN PATENT DOCUMENTS

| WO | 02/053214 | 7/2002 |
| WO | 2009/080775 | 7/2009 |

* cited by examiner

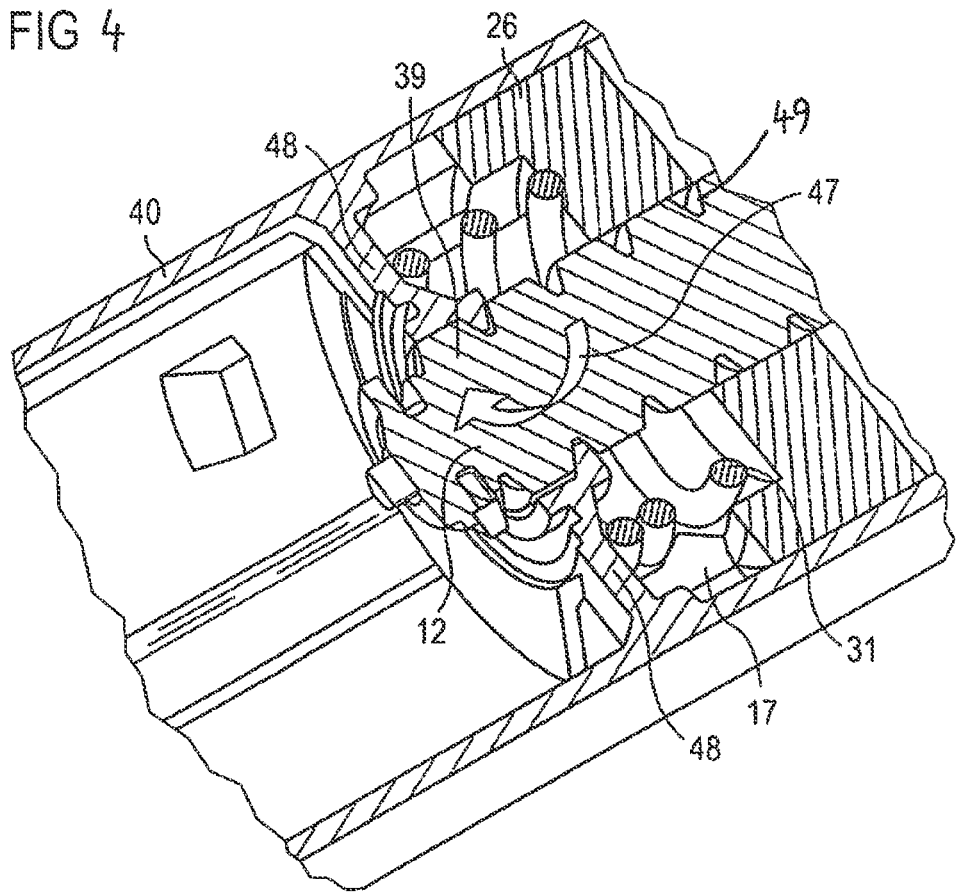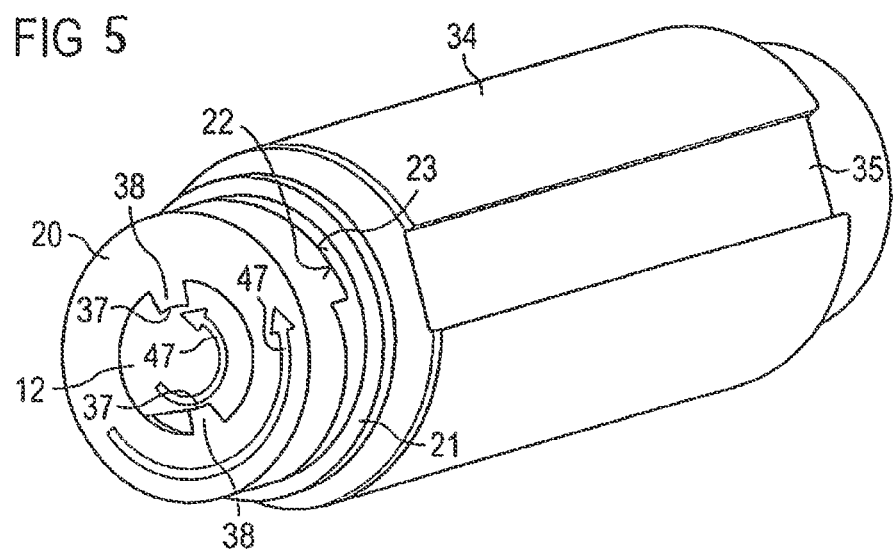

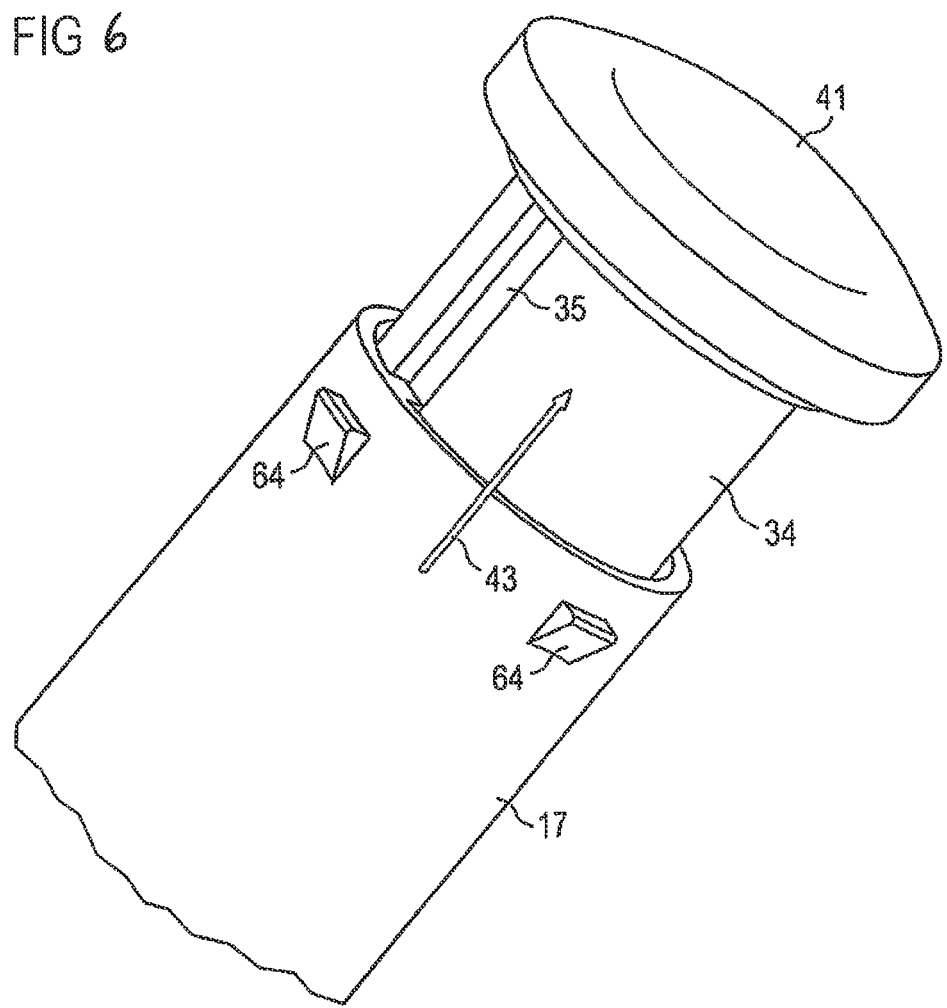

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/059562 filed Jun. 9, 2011, which claims priority to European Patent Application No. 10165635.3 filed on Jun. 11, 2010. The entire disclosure contents of these applications are herewith incorporated by reference into the present application.

BACKGROUND

The present invention relates to a resettable drive mechanism for a drug delivery device and a drug delivery device comprising such a drive mechanism.

In a drug delivery device, a piston within a cartridge that contains drug may be displaced with respect to the cartridge in the distal direction by a piston rod which moves in the distal direction with respect to the cartridge. In order to provide for a reusable device, after the cartridge containing the drug has been emptied, the piston rod often has to be moved back from a distal end position to a proximal starting position. Thereby, a dose of drug can be expelled from the cartridge. U.S. Pat. No. 5,308,340 A and WO 02/053214 A1 describe injection pens, which allow to decrease a selected dose by reversing the set operation.

SUMMARY

It is an object of the invention to disclose a drive mechanism and a drug delivery device offering an easy operation.

This object is achieved by a drive mechanism according to claim 1 and by a drug delivery device according to claim 16. Embodiments derive from the dependent claims.

The drive mechanism for a drug delivery device comprises a housing, a drive member arranged inside the housing, a rotation member, and a dose member. The rotation member is rotatable with respect to the housing. The rotation member is rotatable with respect to the housing and unidirectionally rotationally engaged with the drive member by a clutch. The dose member is engaged with the housing in such a manner that the dose member is movable between a first axial position and a second axial position that is axially spaced from the first axial position. The engagement of the dose member with the housing allows the dose member to move according to a set/deliver path between the first axial position and the second axial position in either direction or to move according to a cancel path from the second axial position to the first axial position. An engagement of the dose member with the rotation member causes the rotation member to rotate when the dose member is moved according to the set/deliver path. The drive member is not rotated when the dose member is moved according to the cancel path. A movement of the dose member according to the cancel path does not cause a movement of the rotation member or generates a rotation of the rotation member with respect to the drive member, which does not rotate.

In an embodiment of the drive mechanism the cancel path implies a helical movement of the dose member with respect to the housing.

In a further embodiment of the drive mechanism the cancel path implies a helical movement of the dose member with respect to the housing and a subsequent rotation of the dose member within the first axial position.

In a further embodiment of the drive mechanism the set/deliver path is connected to the cancel path via a start path located between the second axial position and the cancel path and/or via an end path located between the cancel path and the first axial position.

In a further embodiment of the drive mechanism an engagement member is provided on the rotation member or on the dose member. The dose member is engaged with the rotation member by the engagement member being guided in a thread.

In a further embodiment of the drive mechanism the dose member is engaged with the housing by means of a button in/out spline and a cancel spline. The button in/out spline is arranged according to the set/deliver path, and the cancel spline is arranged according to the cancel path.

In a further embodiment of the drive mechanism a bump feature of the cancel spline makes it more difficult to have the dose member enter the cancel spline than move according to the set/deliver path from the second axial position to the first axial position. There may also be a bump feature at the exit of the cancel spline.

In a further embodiment of the drive mechanism the clutch is formed by an azimuthally arranged series of ramped teeth on the drive member and a corresponding azimuthally arranged further series of ramped teeth on the rotation member.

In a further embodiment of the drive mechanism a stop member is arranged inside the housing, the stop member being axially movable with respect to the housing. A guide feature of the stop member is engaged with the housing and prevents a rotation of the stop member with respect to the housing. The stop member is unidirectionally rotationally engaged with the drive member by a further clutch permitting a rotation of the drive member that is generated by a movement of the dose member from the second axial position to the first axial position according to the set/deliver path.

In a further embodiment of the drive mechanism the further clutch is formed by a further azimuthally arranged series of ramped teeth on the drive member and a corresponding azimuthally arranged further series of ramped teeth on the stop member.

In a further embodiment of the drive mechanism a resilient member exerts a force that tends to keep the drive member and the stop member in contact and to keep the drive member and the rotation member in contact.

In a further embodiment of the drive mechanism a piston rod is arranged inside the housing. The piston rod is rotationally coupled with the drive member and axially movable with respect to the drive member. The drive member may be formed by a tubular sleeve, and the piston rod may be movable through the drive member.

In a further embodiment of the drive mechanism the movement of the dose member from the second axial position to the first axial position according to the set/deliver path generates an axial displacement of the piston rod with respect to the housing by a fixed predetermined distance.

A further embodiment of the drive mechanism comprises a unidirectional rotational engagement between the dose member or a button that is fixed to the dose member and the housing or an insert that is fixed to the housing. The unidirectional rotational engagement may be provided by a ratchet insert with at least one pawl, the ratchet insert being rotationally locked with the dose member, and a ratchet on the housing or insert, the pawl engaging the ratchet.

A drug delivery device may comprise a drive mechanism according to the invention. The drug delivery device may be an injection device, particularly a pen-type injector. The drug delivery device may additionally comprise a cartridge for holding a drug. The cartridge may be inserted in a cartridge holder that may be releasably attached to the housing.

The housing or a drug delivery device comprising the housing has a distal end and a proximal end. The term "distal end" designates that end of the housing, the device or a component thereof which is or is to be arranged closest to a dispensing end of the device. The term "proximal end" designates that end of the housing, the device or a component thereof which is or is to be arranged furthest away from the dispensing end of the device. Accordingly, the "distal direction" is the direction from the proximal end towards the distal end, and the "proximal direction" is the direction from the distal end towards the proximal end.

The drug delivery device may be a disposable or a re-usable device. The device may be configured to dispense a fixed dose of a medicament or drug. The device may be a manually, in particular a non-electrically, operated device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)$_5$-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)$_{25}$, Asp28] Exendin-4(1-39),
des Pro36 [Met(O)14 Trp(O2)$_{25}$, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)$_5$des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)$_6$-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)$_6$-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-5NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A resettable drive mechanism for a drug delivery device preferably comprises a housing with a proximal end and a distal end, the drive member being rotatable with respect to the housing in a second direction for delivering a dose of a drug, the piston rod being adapted to be driven in a distal direction with respect to the housing by the drive member, when the drive member rotates in the second direction, a stop member being adapted to prevent rotation of the drive member in a first direction opposite to the second direction with respect to the housing, when the stop member engages the drive member, and a clutch member movable with respect to the housing between a delivery position and a reset position.

When the clutch member is in the delivery position, the stop member and the drive member are engaged, and the drive member is prevented from rotating in the first direction with respect to the housing. When the clutch member is in the reset position, the drive member and the stop member are disengaged, the drive member is rotatable in the first direction with respect to the housing and the piston rod is movable in the proximal direction with respect to the housing.

The clutch member may be (linearly) displaced with respect to the housing when the clutch member is moved from the delivery position into the reset position or from the reset position into the delivery position. The clutch member may be displaced with respect to one of the drive member and the stop member when the clutch member is moved from the delivery position into the reset position or from the reset position into the delivery position. The other one of the drive member and the stop member may follow movement of the clutch member when the clutch member is moved from the delivery position into the reset position or from the reset position into the delivery position. Via this relative movement, drive member and stop member may be disengaged. The clutch member may be axially displaced with respect to the housing when it is moved from the delivery into the reset position and preferably when it is moved from the delivery position into the reset position. The clutch member may be secured against rotational movement with respect to the housing.

If a clutch member that is movable with respect to the housing between the delivery position and the reset position is provided, a movement of the piston rod in the proximal direction with respect to the housing is facilitated. In particular, since the drive member may be rotated in the first direction with respect to the housing, the drive member may rotate in that direction which is opposite to the one during delivery of the dose of drug without the rotational movement in the first direction being prevented by the stop member. Thus, proximal movement of the piston rod which may cause the drive member to be rotated in the first direction is no longer prevented and resetting of the drive mechanism is facilitated.

The stop member and the drive member may be permanently engaged while the clutch member is in delivery position. The drive member may engage the piston rod. The drive member may be permanently engaged with the piston rod regardless whether the clutch member is in delivery position or in the reset position.

Rotational movement of the drive member may be converted into rotational movement of the piston rod in the same direction. Rotational movement of the piston rod may be converted into displacement of the piston rod with respect to the housing in the distal direction, for example by a threaded engagement of the piston rod with the housing. The piston rod may be displaced in the distal direction with respect to the housing and rotate in the second direction during the distal displacement. The piston rod may be displaced along its rotation axis.

Alternatively, a rotational movement of the drive member may be converted into pure (linear) displacement of the piston rod with respect to the housing. Thus, the piston rod may move translationally with respect to the housing without rotating. A displacement axis of the piston rod may run transversely with respect to the rotation axis around which the drive member rotates.

In an embodiment of the drive mechanism the clutch comprises a resilient member, which may be a spring. The clutch resilient member may be biased when the clutch member is in the delivery position. The clutch resilient member may be fully or partly relaxed when the clutch member is in the reset position.

In another embodiment, the drive mechanism comprises a clutch stop member. The clutch stop member may be movable with respect to the clutch member. The clutch stop member may be removable, in particular from the drive mechanism. The clutch stop member may be arranged to keep, preferably to hold, the clutch member in the delivery position. The clutch stop member may be provided for preventing movement of the clutch member towards the reset position. The clutch stop member may be arranged to counteract the force exerted by the clutch resilient member that tends to move the clutch member in the reset position. The clutch stop member is preferably releasably secured with respect to the housing. If the clutch stop member is removed from the clutch member, e.g. detached from the housing, the clutch member is permitted to move into the reset position after the clutch stop member has been removed. Thus, the clutch stop member may keep the drive mechanism in a delivery state by preventing movement of the clutch member towards the reset position. If the clutch stop member is removed from the clutch member, the clutch member may be moved into the reset position, which movement puts the drive mechanism in a reset state.

The clutch stop member and the clutch resilient member, in combination, may also be provided for an automatically actuated reset mechanism of the drive mechanism. Due to the biased clutch resilient member, the clutch member is moved automatically into a reset position when the clutch stop member is removed.

The rotation member may be adapted to be rotated in the first direction with respect to the housing during setting of a dose of a drug and to be rotated in the second direction with respect to the housing during delivery of the dose. Rotation of the rotation member in the second direction with respect to the housing may be converted into rotation of the drive member in the second direction with respect to the housing, e.g. by mechanical cooperation of the rotation member and the drive member. Rotation of the drive member may be converted into movement of the piston rod with respect to the housing, e.g. by mechanical cooperation of drive member and piston rod and preferably additionally by mechanical cooperation of piston rod and housing, e.g. by a threaded engagement.

According to another embodiment, the drive member, preferably permanently, abuts and/or engages one of or both of stop member and rotation member during (rotational) movement of the rotation member for setting and delivery of the dose. Thus, when the clutch member is in the delivery position, the drive member may, preferably permanently, abut one of or both of rotation member and stop member. The drive member may be coupled to the stop member and/or rotation member during setting and delivery of the dose.

In another embodiment, the drive mechanism comprises a resilient member, which may be a spring. The resilient member may be arranged to keep the stop member and the drive member in abutment and/or engagement. The resilient member may exert a force on one of or both of the drive member and the stop member which force tends to keep the drive member and the stop member in engagement. Preferably, this force has to be overcome for disengaging drive member and stop member.

In another embodiment, the clutch resilient member is a clutch spring member and the resilient member is a spring member. The clutch spring member preferably has a spring strength which is greater than a spring strength of the spring member. Thus, the clutch resilient member may exert a force on the clutch member which overcomes the force exerted by the resilient member by which the stop member and the drive member are kept in abutment and/or engagement. Accordingly, disengaging stop member and drive member is facilitated.

In another embodiment, the stop member and the drive member are arranged to be moved into engagement when the clutch member is moved from the reset position towards the delivery position. The force exerted by the resilient member may assist this movement. An additional external force may be applied for (re-)engaging stop member and drive member. It may be necessary to overcome the force exerted by the clutch resilient member for (re-)engaging stop member and drive member.

In another embodiment, the drive member and the stop member are engaged to form a unidirectional friction clutch mechanism when the clutch member is in the delivery position. Accordingly, relative rotational movement of the drive member with respect to the stop member and, in particular, with respect to the housing in the first direction is prevented when the clutch member is in the delivery position. When the clutch member is in the reset position, the unidirectional clutch is open. Thus, when the clutch member is in the reset position, relative rotational movement between drive member and stop member in the first rotational direction is expediently allowed.

In another embodiment, the drive member and the rotation member are engaged to form a (further) unidirectional friction clutch mechanism when the clutch member is in the delivery position and, preferably, also when the clutch member is in the reset position. This mechanism is expediently configured to prevent relative rotational movement between drive member and rotation member in the second direction.

In another embodiment, the stop member is secured against rotational movement with respect to the housing and the stop member is displaceable with respect to the housing.

In another embodiment, the stop member is arranged to follow movement of the clutch member towards the reset position, thereby disengaging from the drive member.

In another embodiment, the clutch member is arranged to abut the stop member when the clutch member is moved towards the reset position. Preferably, the clutch member carries the stop member with it towards the reset position after having moved into abutment with the stop member.

In an embodiment of a drug delivery device comprising a drive mechanism as described, the cartridge or a cartridge retaining member, which is adapted to retain and/or attach the cartridge to the housing, is the clutch stop member. Thus, the cartridge or the cartridge retaining member may prevent the clutch member from moving into the reset position on account of the force exerted by the clutch resilient member. If the cartridge retaining member or the cartridge is detached from the housing, the clutch member will automatically move into reset position.

BRIEF DESCRIPTION OF THE FIGURES

Further objects, features and advantages of the invention will become apparent from the following detailed description in conjunction with the appended drawings.

FIG. 4 shows a further detail of an embodiment of the drive mechanism including a stop member.

FIG. 5 shows a further detail of an embodiment of the drive mechanism including a rotation member.

FIG. 6 shows a further detail of an embodiment of the drive mechanism including a dose member.

Like elements, elements of the same kind and identically acting elements carry the same reference numerals.

DETAILED DESCRIPTION

Figure 1:
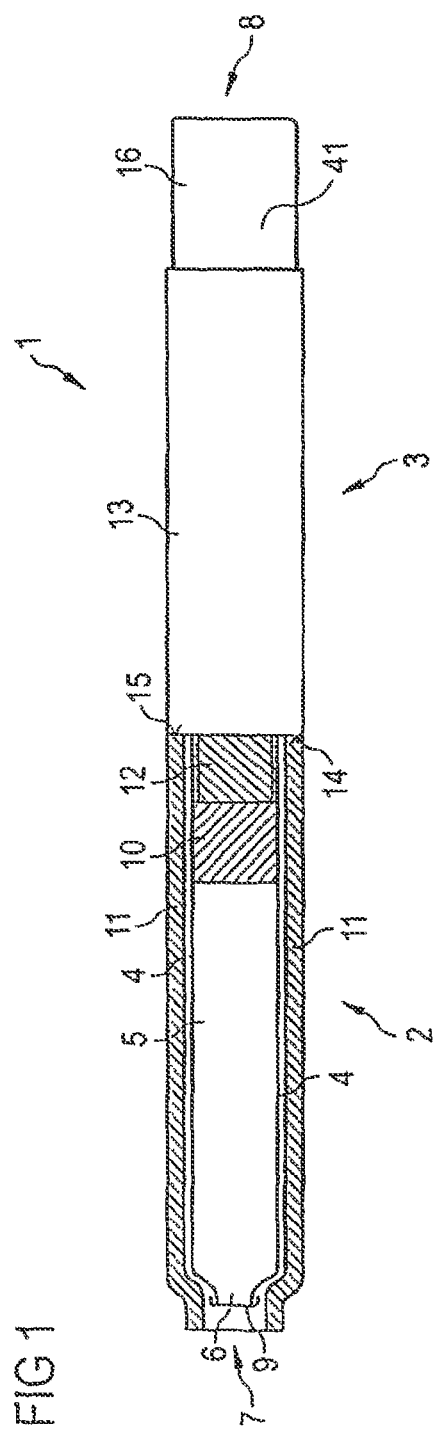
FIG. 1 schematically shows a partly sectional side view of an embodiment of a drug delivery device.
Figure 2:
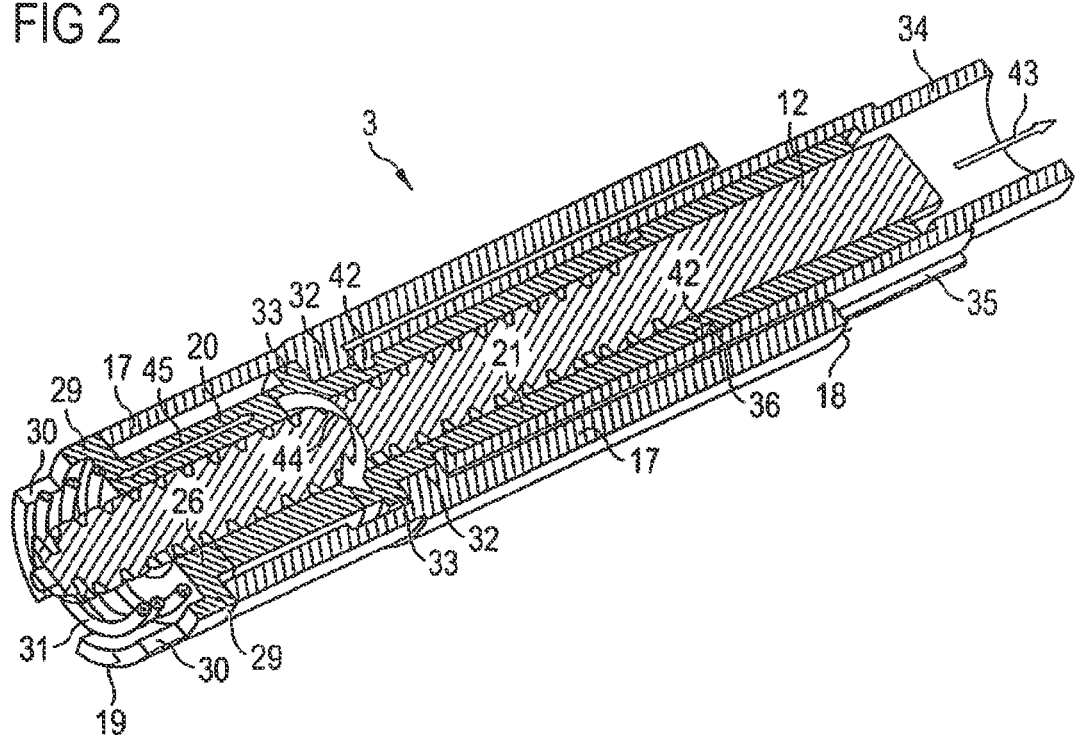
FIG. 2 shows a perspective view of a cross-section of a drive mechanism.
Figure 3:
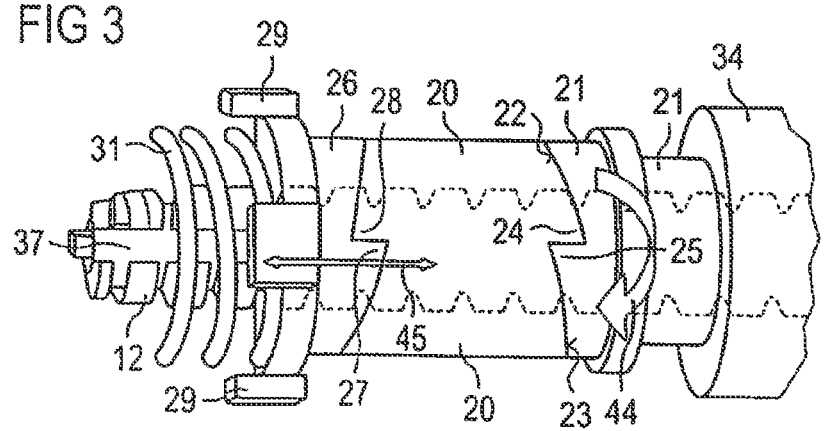
FIG. 3 shows a detail of an embodiment of the drive mechanism including a drive member.
Figure 7:
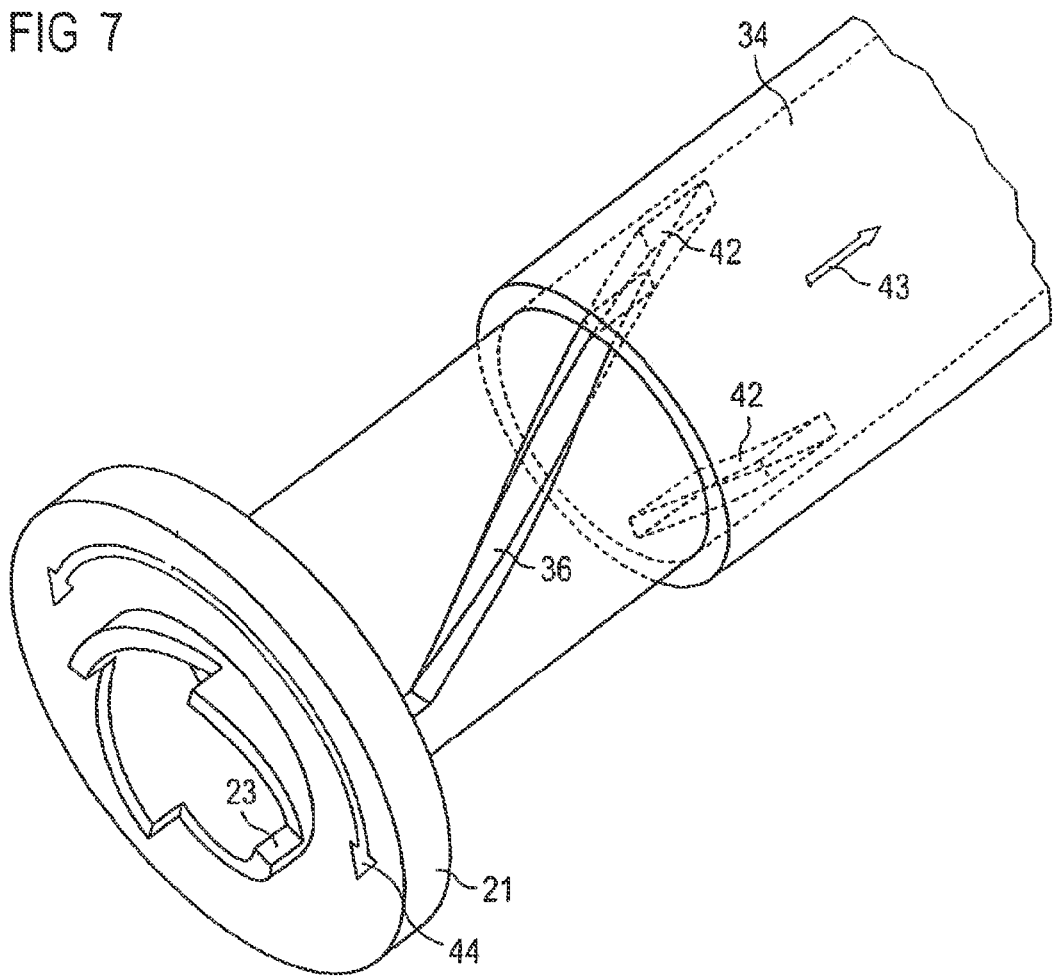
FIG. 7 shows a further detail of an embodiment of the drive mechanism including an engagement between the rotation member and the dose member.

FIG. 1 shows a drug delivery device 1 having a distal end 7 and a proximal end 8 and comprising a cartridge unit 2 and a drive unit 3. The cartridge unit 2 comprises a cartridge 4. Drug 5 is retained in the cartridge 4. The drug 5 is preferably liquid drug. The cartridge 4 preferably comprises a plurality of doses of the drug 5. The drug 5 may comprise insulin, heparin, or growth hormones, for example. The cartridge 4 has an outlet 6 at its distal end. Drug 5 can be dispensed from the cartridge through outlet 6. The device 1 may be a pen-type device, in particular a pen-type injector. The device 1 may be a disposable or a reusable device. The device 1 may be a device configured to dispense fixed doses of the drug. The device 1 may be a needle-based or a needle free device. The device 1 may be an injection device.

The outlet 6 may be covered by a membrane 9, which protects drug 5 against external influences during storage of the cartridge. For drug delivery, membrane 9 may be opened, e.g. pierced. For example, membrane 9 may be pierced by a needle unit (not explicitly shown). The needle unit may be (releasably) attached to the distal end of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the drug 5 within the cartridge. The piston 10 expediently seals the interior of the cartridge 4 proximally. Movement of the piston 10 with respect to the cartridge 4 in the distal direction causes drug 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive unit 3.

The cartridge unit 2 and the drive unit 3 are secured to one another, preferably releasably secured. A cartridge unit 2 which is releasably secured to the drive unit may be detached from the drive unit 3, for example in order to allow for providing for a new cartridge 4, if all of the doses of drug which once were in the cartridge formerly attached to the drive unit 3 have already been dispensed. The cartridge retaining member 11 may be releasably secured to the drive unit 3 via a thread, for example.

Alternatively, the cartridge retaining member 11 may be dispensed with. It is particularly expedient, in this case, to apply a robust cartridge 4 and to attach the cartridge directly to the drive unit 3.

The drive unit 3 is configured for transferring force, preferably user-exerted force, particularly preferably manually exerted force, to the piston 10 for displacing the piston 10 with respect to the cartridge 4 in the distal direction. A dose of drug may be dispensed from the cartridge in this way. The size of the delivered dose may be determined by the distance by which the piston 10 is displaced with respect to the cartridge 4 in the distal direction.

The drive unit 3 comprises a drive mechanism. The drive mechanism comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rod rotates and is displaced with respect to the housing, the bearing member is preferably only displaced, i.e. does not rotate. The piston rod may be bounded by the bearing member.

The drive unit 3 comprises a housing 13 which may be part of the drive mechanism. The piston rod 12 may be retained in the housing. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the drug delivery device, preferably from the drive member to the piston, for example for the purpose of discharging/dispensing an injectable product. Said piston rod may be flexible or not. It may be a simple rod, a lead-screw, a rack and pinion system, a worm gear system, or the like. "piston rod" shall further mean a component having a circular or non-circular cross-section. It may be made of any suitable material known by a person skilled in the art and may be of unitary or multipart construction.

The drive unit 3 comprises a dose part 16. The dose part 16 is movable with respect to the housing 13. The dose part 16 may be movable in the proximal direction with respect to the housing for setting of a dose of the drug 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing.

The device 1 may be a manually, in particular non-electrically, driven device. The (user-applied) force which causes the dose part 16 to be moved with respect to the housing 13 in the distal direction may be transferred to the piston rod 12 by the drive mechanism. For this purpose, other elements of the drive mechanism may be provided which are not explicitly shown in FIG. 1. When the dose part is moved in the proximal direction with respect to the housing for setting a dose, a movement of the piston rod 12 with respect to the housing 13 is preferably prevented.

Embodiments of a drive mechanism which are suitable to be provided in the drug delivery device 1 as it was described above are described in more detail below.

Embodiments of a drive mechanism which is suitable for being implemented in the drug delivery device 1 as described above are described in connection with FIGS. 2 to 7.

The drive mechanism comprises a housing part 17. The housing part 17 has a proximal end 18 and a distal end 19. The housing part 17 may be (outer) housing 13 of FIG. 1, a part thereof or an insert within housing 13, which insert is preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements 64, for example snap-fit elements, for fixing housing part 17 to housing 13 (cf. FIG. 6).

The piston rod 12 is retained in the housing 13, preferably within housing part 17. The piston rod 12 is driven in the distal direction with respect to the housing part 17 during dose delivery.

The drive mechanism furthermore comprises a drive member 20. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member, for example rotational movement in a second direction may be converted into distal movement of the piston rod 12 with respect to the housing part 17. This is explained in more detail below.

The drive mechanism furthermore comprises a rotation member 21. The rotation member 21 is rotatable with respect to the housing part 17 in a first direction, in particular for setting of a dose of the drug, and in a second direction, in particular for delivering the set dose. The second direction is opposite to the first direction. The first direction may be counter-clockwise and the second direction may be clockwise as seen from the proximal end of the device, for example.

Drive member, rotation member and/or piston rod are preferably configured to be rotatable about a (common) rotation axis. The rotation axis may extend through drive member, rotation member and/or piston rod. The rotation axis may be the main longitudinal axis of the piston rod. The rotation axis may run between the proximal end and the distal end of the housing part 17.

The rotation member 21 is coupled to the drive member 20 by an uni-directional clutch mechanism, in particular a friction clutch mechanism. This clutch mechanism permits rotational movement of the rotation member 21 with respect to the drive member 20 when the rotation member rotates in the first direction with respect to the housing part 17. The clutch mechanism prevents rotational movement of the rotation member 21 with respect to the drive member 20, when the rotation member rotates in the second direction with respect to the housing part 17. The drive member 20 may thus follow rotational movement of the rotation member 21 in the second direction with respect to the housing part 17.

The drive member 20 is arranged to abut and/or engage the rotation member and, in particular, engages rotation member 21. The drive member 20 comprises a toothing 22. Toothing 22 may be provided at one end of the drive member, e.g. its proximal end. The rotation member comprises a toothing 23. Toothings 22 and 23 face one another. Toothing 23 may be provided at one end of the rotation member which end faces the drive member 20, e.g. at the distal end of the rotation member. Toothing 22 comprises a plurality of teeth 24. Toothing 23 comprises a plurality of teeth 25. Teeth 24 and/or 25 may extend and preferably may be oriented along the rotation axis. Toothings 22 and 23 may be configured to mate with one another. The rotation member and the drive member may engage each other by toothings 22 and 23 being in engagement.

The teeth 24 and/or teeth 25 may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member is rotated further on in the second direction, the steep sides stay in abutment and drive member 20 follows the rotation of rotation member 21. When the rotation member rotates in the first direction, the ramp of the teeth—which ramps, in particular, run obliquely with respect to the rotation axis—slide along each other and, in consequence, the rotation member 21 may rotate with respect to the drive member 20.

The drive mechanism furthermore comprises a stop member 26. The drive member 20 may be arranged between the stop member 26 and the rotation member 21. The stop member 26 is configured for preventing rotational movement of the drive member 20 in the first direction with respect to the housing part 17 during setting of a dose, i.e. when the rotation member 21 rotates in the first direction. Thus, the rotation member 21 may rotate in the first direction with respect to the housing part 17, whereas the drive member 20 and the stop member 26 do not rotate.

The stop member 26 is coupled to the drive member 20 by another uni-directional clutch mechanism, in particular a friction clutch mechanism. This clutch mechanism prevents rotational movement of the drive member 20 with respect to the stop member 26 when the rotation member 21 rotates in the first direction with respect to the housing part 17. The clutch mechanism permits rotational movement of the drive member 20 with respect to the stop member 26, when the rotation member 21 rotates in the second direction with respect to the housing part 17.

Thus, the rotation member 21 may rotate with respect to the drive member 20 and the stop member 26 in the first direction during setting of the dose, with rotation of the drive member 20 being prevented by its interaction with the stop member 26, and rotation member 21 as well as drive member 20 may rotate with respect to the stop member 26 in the second direction during delivery of the dose.

The stop member may be arranged to abut and/or engage the drive member during setting of the dose and, preferably, during delivery of the dose. The stop member 26 is provided with teeth 27 on that side of the stop member 26 which faces the drive member 20. The teeth 27 may be ramp-shaped with a steep side and a less steep ramp. The teeth 27 may be disposed azimuthally along the perimeter of the stop member 26. The teeth 27 may extend and preferably may be oriented along the rotation axis.

The drive member 20 is provided with teeth 28 on that side of the drive member 20 which faces the stop member 26. The teeth 28 may extend and preferably be oriented along the rotation axis. The teeth 24 and the teeth 28 of the drive member 20 are oppositely disposed. The teeth 24 may be configured corresponding to the teeth 25 of the rotation member 21. The teeth 28 may be configured corresponding to the teeth 27 of the stop member 26. The teeth 27 and 28 may face one another and may especially mate with one another. The teeth 27 and 28, in particular the steep sides of the teeth, cooperate, e.g. abut, for preventing rotation of the drive member 20 with respect to the housing part 17 and, in particular, with respect to the stop member 26 in the first direction.

Stop member 26 is preferably secured against rotational movement, particularly preferably permanently secured against rotational movement, with respect to the housing part 17. Stop member 26 may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 to 5. A guide feature 29 cooperates with a guide slot 30 to prevent rotational movement of the stop member with respect to the housing part 17, with axial movement of the stop member 26 with respect to the housing being allowed. The axial movement of the stop member 26 may compensate for play between components of the drive mechanism during operation.

From the group comprising the drive member 20, the stop member 26 and the rotation member 21 one or more members, preferably two members or three members, may be axially displaceable with respect to the housing part 17 and, preferably, with respect to the piston rod 12. Therein, the drive member and another one of the recited members may be axially displaceable with respect to the housing. The remaining member may be secured against axial displacement or may also be axially displaceable during operation of the drive mechanism for drug delivery. Accordingly, if the drive member and the stop member are axially displaceable, the rotation member may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member. Alternatively, the distance may be greater than the (maximum) depth of a tooth of the respective toothing.

Furthermore, the drive mechanism comprises a resilient member 31, preferably a spring member. The resilient member 31 may be biased during drug delivery operation of the drive mechanism. The resilient member may provide for a force that tends to keep the drive member 20 in engagement with the stop member 26 and/or the rotation member 21. The force may be exerted along the rotation axis. In the situation shown in FIGS. 2 and 3, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the drug. Alternatively or additionally, the resilient member 31 may keep the drive member 20 and the rotation member 26 in (permanent) mechanical contact, preferably abutment, with each other during setting and delivery of a dose of the drug.

The resilient member 31 may be integrated within stop member 26 or a separate component. The resilient member 31 may be arranged on the distal end side of the stop member 26.

The drive mechanism furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member with the drive member and of the drive member with the stop member during setting and delivery of drug is facilitated in this way.

The rotation member 21 has an (radially) outwardly protruding member 33, for example a flange portion. The protruding member 33 is expediently provided for abutting support member 32, in particular the distal end side of support member 32.

Another support 48 (cf. FIG. 4) may be provided for providing a counterforce to the force exerted by the resilient member 31. Support 48 is arranged on that side of the drive member 20 which is remote from the rotation member 21. Support 48 is arranged on that side of the stop member 26 which is remote from the support member 32. The support 48 may be arranged to abut the resilient member 31. The support 48 may be secured against axial and rotational movement with respect to the housing part 17, with respect to the housing 13 or integrated into the housing 13, for example into (additional) housing part 40 (cf. FIG. 4).

The drive mechanism furthermore comprises a dose member 34. Dose member 34 may be dose part 16 or may be a part of the dose part 16 of FIG. 1. Dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13. The dose member 34 may be displaced with respect to housing part 17 preferably only axially along and/or rotationally around the rotation axis.

Dose member 34 may be moved in the proximal direction and in the distal direction with respect to rotation member 21. Dose member 34 is arranged to be coupleable and is preferably (permanently) coupled to rotation member 21 such that movement of the dose member, e.g. in the proximal direction with respect to the housing part 17, for setting a dose of the drug is converted into rotational movement of the rotation member in the first direction and movement of the dose member, e.g. in the distal direction with respect to the housing part 17, for delivering the dose is converted into rotational movement of the rotation member 21 in the second direction opposite to the first direction.

The rotation member 21 may be arranged inside the dose member 34, or the dose member 34 may be arranged inside the rotation member 21. If the rotation member 21 is arranged inside the dose member 34, the rotation member 21 may be provided with an (outer) thread 36, which may be engaged with an engagement member 42 or with a plurality of engagement members 42 of the dose member 34, preferably on an inner wall of the dose member 34. The engagement member 42 may be a lug or a thread or a part of a thread, for example. If the dose member 34 is arranged inside the rotation member 21, the dose member 34 may be provided with an (outer) thread 51 (cf. FIGS. 8 to 10), which may be engaged with an engagement member 50 or with a plurality of engagement members 50 of the rotation member 21, preferably on an inner wall of the rotation member 21. Thus, dose member 34 and rotation member 21 may be threadedly coupled, in particularly threadedly engaged.

The rotation member 21, the drive member 20, the stop member 26 and/or the dose member 34 may be or may comprise a respective sleeve. The piston rod 12 may be arranged to be driven and, in particular, may be driven through one of, more of or all of those sleeves. The piston rod 12 may run through one of, more of or all of those sleeves.

The drive member 20 and the piston rod 12 are configured for rotational movement of the drive member 20 with respect to the housing being converted into rotational movement of the piston rod with respect to the housing. The drive member 20 may engage the piston rod 12. The piston rod 12 is displaceable with respect to the drive member 20 along a displacement axis, which is parallel to the rotation axis. The drive member 20 may be splined to the piston rod 12, for example.

The piston rod 12 is threadedly coupled to the housing 13. The piston rod 12 may be provided with an outer thread 49, for example. The piston rod 12 may extend through and be engaged with a (part) thread in opening 39 which is provided in housing part 40, for example in support 48 (cf. FIG. 4). Housing part 40 may be formed integrally with housing part 17, may be a housing part fixed thereto or may be a housing part secured separately from housing part 17 to housing 13.

The piston rod 12 comprises an engagement track 37, preferably two oppositely disposed engagement tracks, on the outside. The (respective) engagement track 37 may interrupt thread 49. The (respective) engagement track 37 preferably extends along the axis along which the piston rod is displaceable with respect to the housing and, in particular, with respect to the drive member.

Rotational movement of the drive member 20 with respect to the housing may thus be converted into rotational movement of the piston rod 12 with respect to the housing and the rotational movement of the piston rod 12 is, on account of the threaded engagement of the piston rod and the housing (part), converted into movement of the piston rod with respect to the housing in the distal direction.

The dose part 16 (cf. FIG. 1) may comprise a button 41 (cf. FIG. 6). Button 41 may be configured to be gripped by a user. Button 41 may be arranged and connected to the dose member 34 at the proximal end. Button 41 and dose member 34 may be unitary.

The operation of the drive mechanism will be described in the following. To set a dose, dose member 34 is moved in the proximal direction (arrow 43 in FIG. 2) with respect to the housing part 17 (first type of movement). To do so, the user may grip button 41 and pull it in the proximal direction. Dose member 34 moves proximally also with respect to the rotation member 21. Proximal movement of the rotation member is prevented by support member 32 which abuts protruding member 33 of rotation member 21. Consequently, the proximal movement of dose member 34 with respect to the housing part 17 is converted into rotational movement of the rotation member 21 in the first direction (arrow 44 in FIG. 2) with respect to the housing part 17, in particular on account of the engagement of dose member 34 and rotation member 21. Thus, the rotation member 21 rotates in the first direction with respect to the housing, which in the present embodiment is counter-clockwise as seen from the proximal end of the rotation member 21. The rotation member 21 also rotates with respect to the drive member 20 and to the stop member 26. The drive member 20 is prevented from rotating in the first direction by interaction with the stop member 26, e.g. by interlocking of teeth 27 and 28. As the piston rod 12 is coupled to the drive member 20 and rotation in the first direction of the drive member would cause the piston rod to travel in the proximal direction, the piston rod 12 is prevented from being driven in the proximal direction by interaction of stop member 26 and drive member 20. By preventing the piston rod 12 from moving during dose setting dose accuracy can be increased.

When the rotation member 21 rotates in the first direction, the ramps of the teeth 25 of the rotation member 21 slide along the ramps of the teeth 24 of the drive member 20. Thus, the teeth 25 of the rotation member 21 turn around the rotation axis until they engage the next teeth of the drive member 20. During this movement, the drive member 20 and, in particular, the stop member 26 are displaced along the rotation axis with respect to piston rod 12 and housing by a distance determined by, preferably equal to, the depth of a tooth. When the teeth of the rotation member 21 engage the next teeth of the drive member 20, the force exerted by the resilient member 31 moves the drive member 20 and, in particular, the stop member 26 back along the rotation axis into the axial start position. An according movement of the stop member 26 and the drive member 20 in the distal direction and back into the proximal direction is indicated by the double arrow 45 in FIGS. 2 and 3. A tooth of the rotation member which engages the next tooth of the drive member may cause an audible and/or tactile feedback to the user.

The drive mechanism is especially suitable for a fixed-dose device. The size of the fixed dose of drug which is to be delivered is preferably determined by the distribution of the teeth of the respective toothings in the drive member, rotation member and stop member. The rotation member 21 may especially have to be rotated over only one tooth of the drive member 20 in order to set a fixed dose. The number of teeth in the drive member 20 over which the rotation member 21 rotates during dose setting may determine the size of the dose which is actually delivered. The dose member and the rotation member may be adapted to one another such that the rotation member may rotate only by one tooth for a fixed dose device and by more than one tooth for a variable dose device.

After the dose has been set, the dose part 16 and with it the dose member 34 is moved (pushed) by the user in the distal direction with respect to housing part 17 (opposite direction of arrow 43; second type of movement). Thus, the dose member 34 is moved in the distal direction with respect to the housing part 17. The rotation member 21 accordingly rotates in the second direction, which is opposite to the first direction, with respect to the housing (opposite direction of arrow 44). The drive member 20 follows rotational movement of the rotation member 21 in the second direction. Rotational movement of the drive member 20 in the second direction is converted into rotational movement of the piston rod 12 in the second direction, which movement, in turn, is converted into movement of the piston rod 12 in the distal direction. Accordingly, the piston 10 may be displaced in the distal direction with respect to the cartridge 4 and a dose of drug 5 is dispensed from the cartridge the amount of which corresponds to the previously set dose.

During dose delivery, the toothings 22 and 23 interlock and the ramps of the teeth 28 of the drive member 20 slide along the ramps of the teeth 27 of the stop member 26. This movement is similar to the relative rotational movement of the rotation member and the drive member described above, but for an opposite rotation direction. The stop member 26 is thereby displaced in the distal direction with respect to the drive member 20 by a distance corresponding to the depth of a tooth 27 of the stop member 26. The resilient member 31 forces the stop member 26 back into the axial start position, when the next teeth 28 of the drive member 20 are engaged by the teeth 27 of the stop member 26. A tooth of the drive member which engages the next tooth of the stop member may cause an audible and/or tactile feedback to the user.

Figure 8:
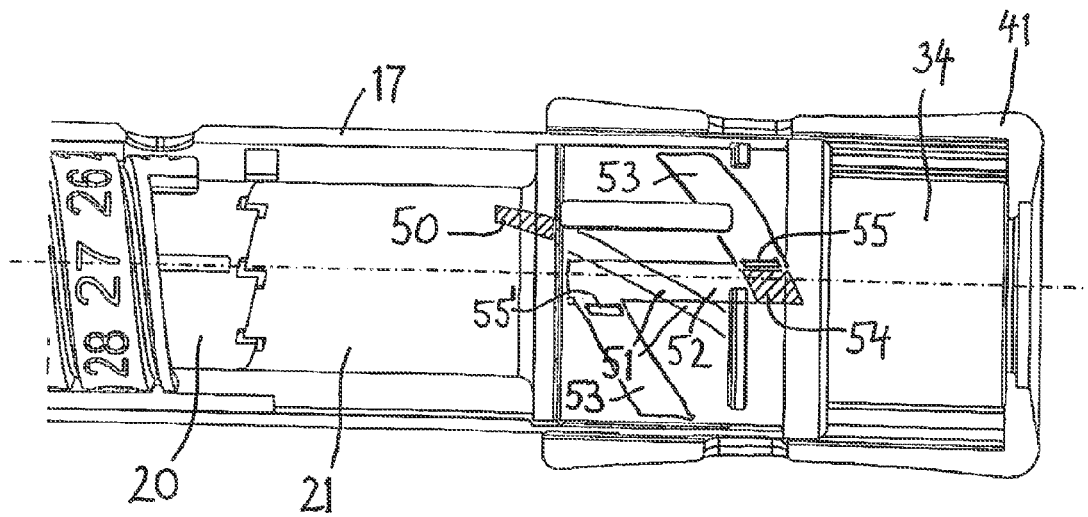
FIG. 8 shows an arrangement of the drive mechanism after a setting of a dose, the dose member being in the second axial position.

FIG. 8 shows an arrangement of the proximal portion of the drive mechanism after a setting of a dose. The figure shows a housing part 17 at the proximal end. Before the setting of a dose, the dose member 34 is at a first axial position. To set a dose, the dose member 34 is drawn out of the housing 13 in the proximal direction from the first axial position into a second axial position as shown in FIG. 8. This movement of the dose member 34 from the first axial position to the second axial position will be called first type of movement. It is performed along a set/deliver path provided by an engagement of the dose member 34 with the housing 13 or housing part 17.

In the embodiment shown in FIG. 8 the dose member 34 is arranged in the rotation member 21, which is formed as a sleeve surrounding the most distal part of the dose member 34. Instead, as described above, the dose member 34 can be a sleeve surrounding the rotation member 21. The rotation member 21 is coupled with the dose member 34 in such a manner that the axial movement of the dose member 34 rotates the rotation member 21. In the embodiment shown in FIG. 8, the rotation of the rotation member 21 during setting is clockwise as seen from the proximal end. Apart from the small reciprocating movement caused by the toothed engagement with the drive member 20, the rotation member 21 stays essentially fixed in the axial direction.

The rotation of the rotation member 21 may be effected by an engagement member 50, which is guided in a screw thread 51. The engagement member 50 can be formed on the inner wall of the rotation member 21 as an integral part thereof, for instance, and the thread 51 can be provided on the outer surface of the cylindrical dose member 34. Instead, the engagement member 50 can be formed on the outer surface of the dose member 34, and the thread 51 be located on the inner wall of the rotation member 21.

A rotation of the dose member 34 may be prevented during a set operation by a spline, which will be called button in/out spline 52 in the following. The button in/out spline 52 may be provided on the housing part 17, for instance, and preferably extends in the axial direction or at least primarily in the axial direction. A guide feature 54 of the dose member 34 is guided in the button in/out spline 52 during the first type of movement. Thus the dose member 34 is moved according to the set/deliver path without being rotated with respect to the housing 13 or housing part 17. The same applies to the opposite movement of the dose member 34 during the delivery of the set dose, when the guide feature 54 moves back through the button in/out spline 52, again according to the set/deliver path, but in reverse direction. This movement of the dose member 34 will be called second type of movement.

The first and second types of movement can be guided along the set/deliver path by other guide features than the ones described above. Particularly, a guide feature can be provided on the housing 13 or part of the housing 17, and a corresponding button in/out spline may be provided on the dose member 34.

The setting of a dose can be cancelled by a third type of movement, by which the dose member 34 is moved back into its first axial position along a cancel path without rotating the drive member 20. This is achieved by a further coupling feature between the dose member 34 and the housing 13 or housing part 17. In the embodiment shown in FIG. 8, the further coupling feature is provided by the guide feature 54 and a cancel spline 53, which is helically wound and may be arranged on the inner surface of the housing part 17, for example.

After the setting of a dose, the dose member 34 need not be pushed axially in the distal direction to deliver the set dose, but it may be moved according to the third type of movement along the cancel path, guided by the cancel spline 53. In the latter case, the movement of the dose member 34 does not cause a movement of the rotation member 21, or it generates a rotation of the rotation member 21 that does not rotate the drive member 20 with respect to the housing 13. The former may be the case if the pitch of the screw thread 51 producing the helical movement of the rotation member 21 with respect to the dose member 34 is equal to the pitch of the cancel spline 53. The latter may be the case if the pitch of the cancel spline 53 is smaller than the pitch of the screw thread 51, while both helices have the same sense of rotation. In this case the rotation member 21 rotates during cancelling in the same direction as during setting, but at a smaller angular velocity than the dose member 34. The rotation member 21 rotates relatively to the drive member 20, which is fixed with respect to the housing 13 by its unidirectional engagement with the stop member 26, in order to avoid an injection during cancelling.

A bump feature 55 may be provided at the beginning of the cancel spline 53 to cause the second type of movement to be more easily performed than the third type of movement. To this end, the bump feature 55 may produce a resistance that impedes the guide feature 54 to enter the cancel spline 53. Furthermore, the bump feature 55 may produce a tactile resistance, which obliges the user to start a cancellation deliberately by a movement of the dose member 34 against this resistance. A similar bump feature 55' may be arranged at the exit of the cancel spline 53, as shown in FIG. 8.

The third type of movement may be concluded when the dose member 34 is again in the first axial position, which it occupied before the setting of the dose. The dose member 34 may have been rotated with respect to its initial position. If there are two parallel button in/out splines 52 on opposite sides of the dose member 34, for example, the third type of movement may cause a rotation of the dose member by 180°, for example. When the setting of a dose is repeated after a cancellation, each guide feature 54 moves along the button in/out spline 52 that is opposite to the one that had been used in the previous set operation. In other embodiments, the third type of movement may be concluded with a rotation of the dose member 34 within its first axial position by 180° in the opposite direction with respect to the rotation during the preceding helical movement. This may be required to restore the initial position completely and to permit the guide feature 54 to enter the same button in/out spline 52 as before. This may be necessary, for instance, if there is only one button in/out spline 52.

Figure 9:
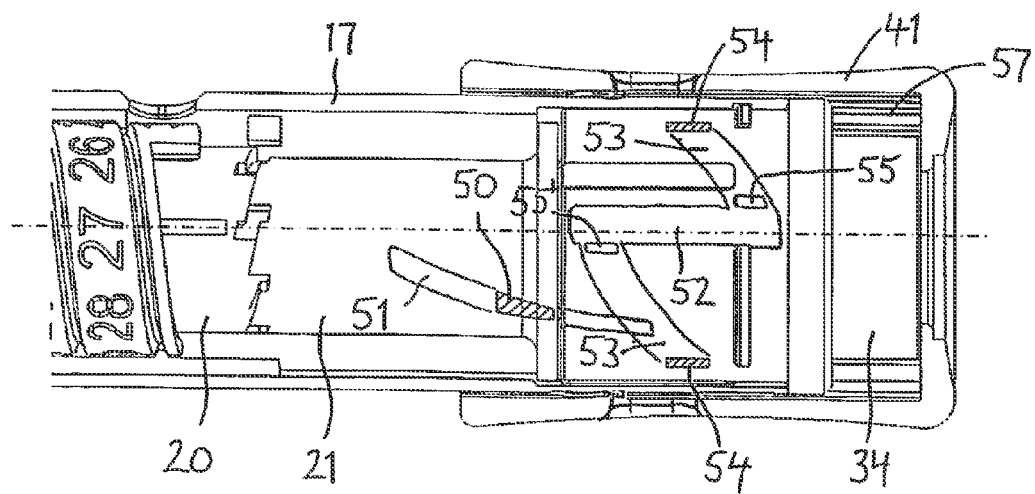
FIG. 9 shows an arrangement of the drive mechanism after a partial cancellation of the setting, the dose member being between the first and the second axial position.

FIG. 9 shows an arrangement of the proximal portion of the drive mechanism according to FIG. 8 after a partial cancellation of the setting. The dose member 34 is shown half way between its first and its second axial position. In the embodiment of FIG. 9, there are two guide features 54 and two parallel button in/out splines 52 on opposite sides of the dose member 34. Each button in/out spline 52 is connected to one of two cancel splines 53, which are also arranged on opposite sides of the dose member 34. FIG. 9 shows the two guide features 54 on opposite sides of the dose member 34. One of the cancel splines 53, which are part of the housing or the housing part 17 in this embodiment, is shown in the same position as in FIG. 8. The dose member 34 is rotated by 90° relative to its position shown in FIG. 8.

Figure 10:
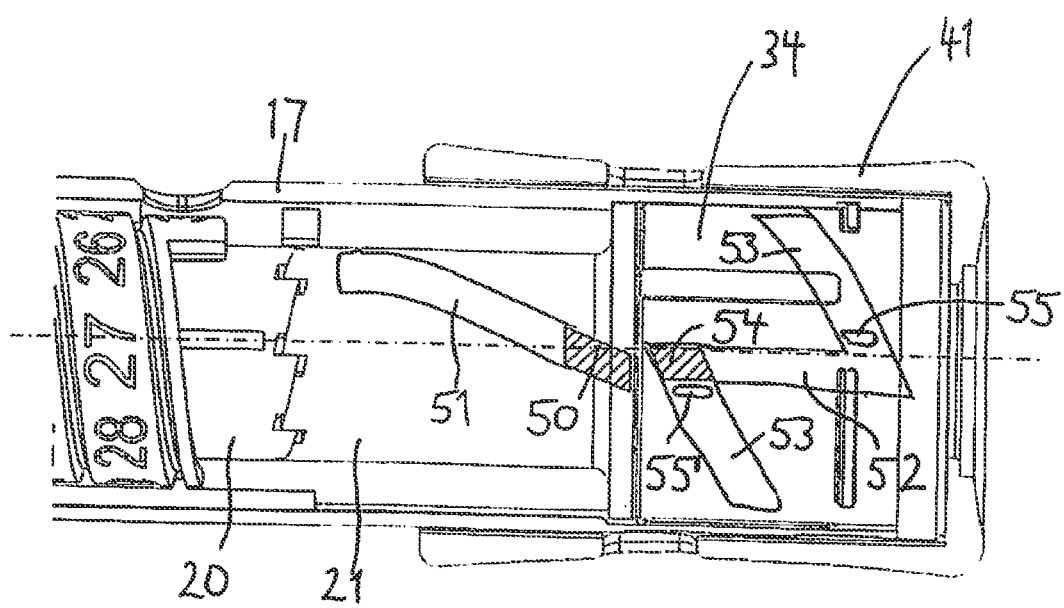
FIG. 10 shows an arrangement of the drive mechanism after a complete cancellation of the setting, the dose member being in the first axial position.

FIG. 10 shows an arrangement of the proximal portion of the drive mechanism according to FIGS. 8 and 9 after a complete cancellation of the setting. The dose member 34 is in its first axial position, rotated by 180° relative to its position shown in FIG. 8. The dose member 34 may then again be pulled out of the housing in the proximal direction to set a dose by the first type of movement, until the dose member 34 reaches the second axial position. During this movement, the guide features 54 move along the opposite button in/out splines 52 according to the set/deliver path. A repeated cancellation causes a repeated rotation of the dose member 34 by 180°. If the set dose is delivered by pushing the dose member 34 in the distal direction back into its first axial position, according to the second type of movement, the dose member 34 is not rotated with respect to the housing.

Figure 11:
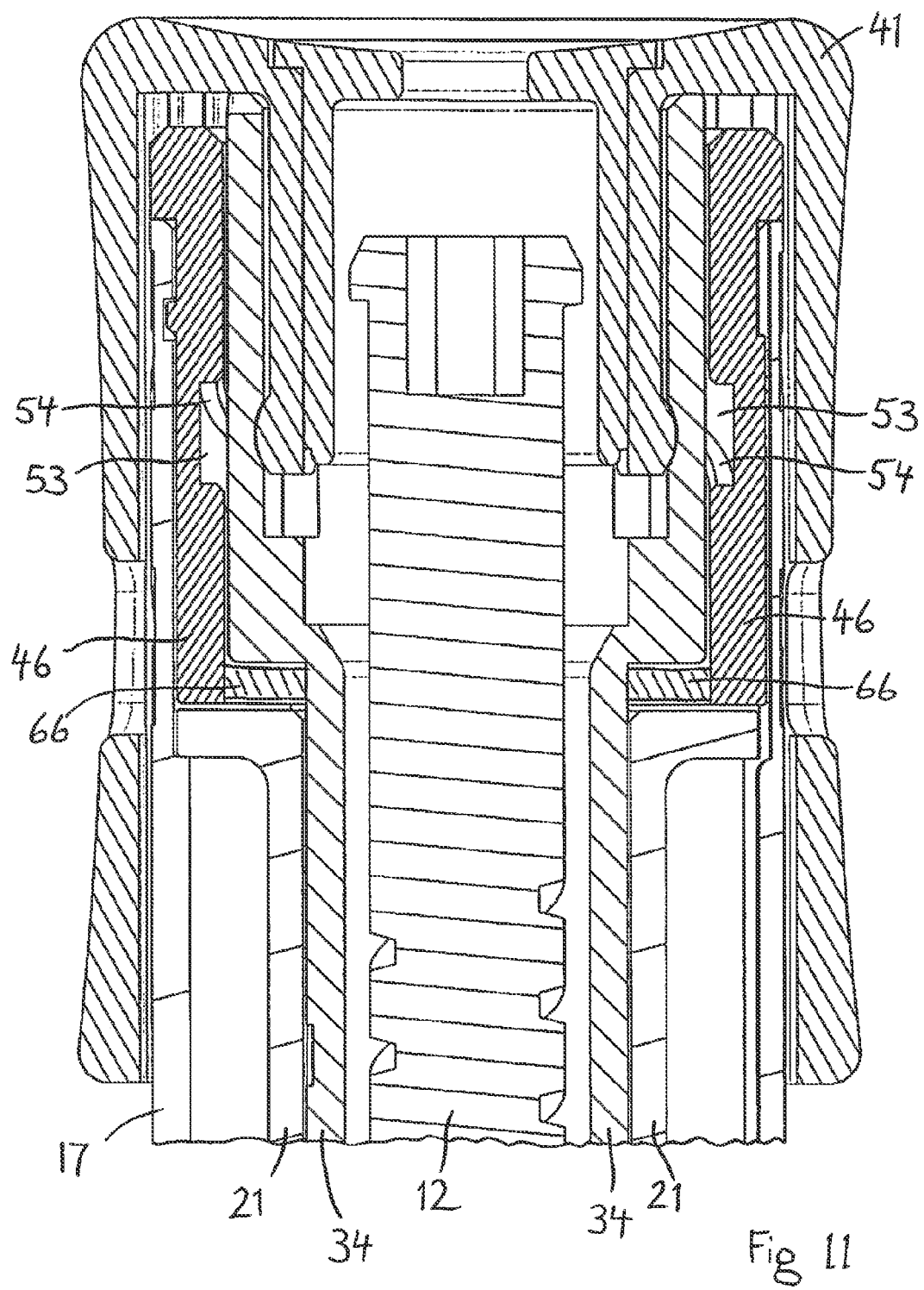
FIG. 11 shows a detailed cross-sectional view of the proximal part of the drive mechanism.
Figure 16:
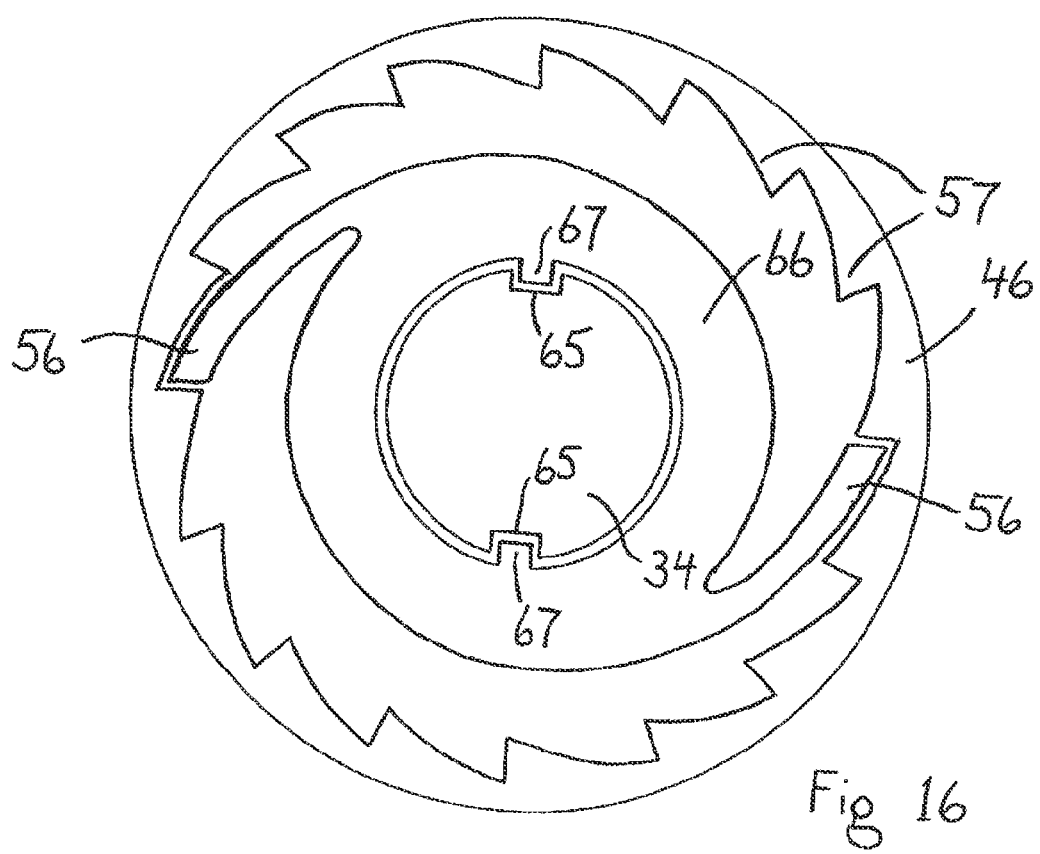
FIG. 16 shows a schematic cross-section of a ratcheting mechanism between the dose member and the housing.

FIG. 11 shows a detailed cross-sectional view of the proximal part of the drive mechanism for an embodiment, which is provided with an insert 46 of the housing 13 or housing part 17. The insert 46 functions as a lock ring, which maintains the rotation member 21 in its axial position with respect to the housing. The insert 46 may be provided with the button in/out spline 52 and the cancel spline 53 as shown in FIG. 11. Instead, the splines can be provided in the housing or in another housing part. The guide feature 54 of the dose member 34 engages the button in/out spline 52 or the cancel spline 53. A ratchet insert 66, which will be described below in conjunction with FIG. 16, may be arranged between the insert 46 and the dose member 34. In the embodiment of FIG. 11, the rotation member 21 surrounds the dose member 34. The rotation member 21 may instead be arranged within the dose member 34. The rotation member 21 and the dose member 34 may be sleeves arranged around the piston rod 12. The button 41 can be an integral part of the dose member 34 or a separate part, which is axially fastened to the dose member 34, as in the embodiment shown in FIG. 11. When the button 41 is pulled, the dose member 34 is simultaneously moved in the proximal direction.

Figure 12:
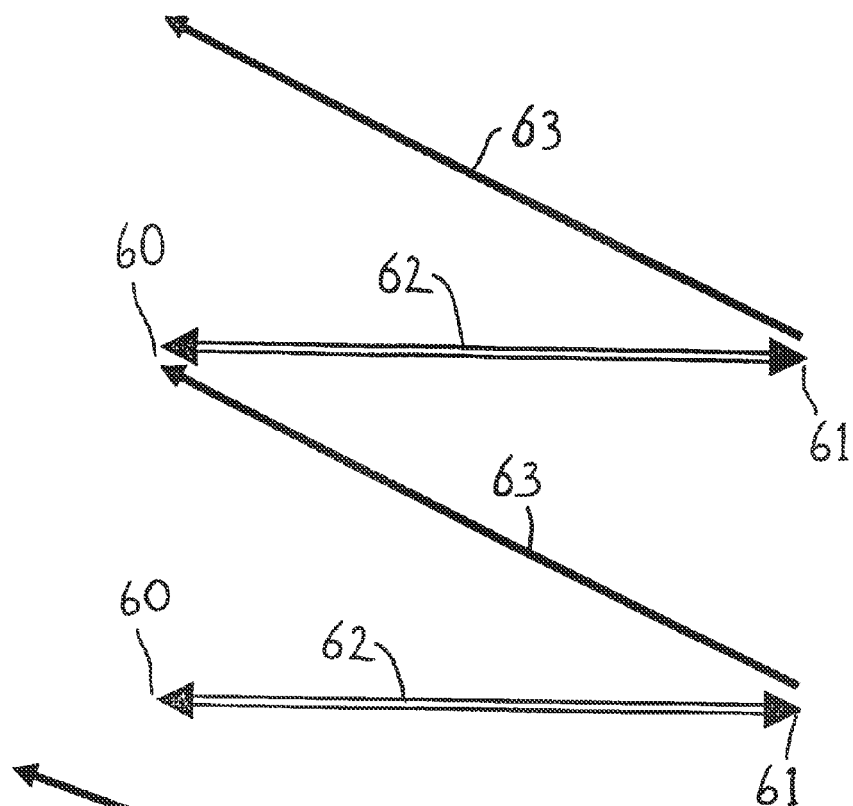
FIG. 12 shows an example of an arrangement of a set/deliver path and a cancel path in a planar evolution.

FIG. 12 shows an example of an arrangement of the set/deliver path 62 and the cancel path 63 in a planar evolution, corresponding to a rotation of the device by 360° around its core axis arranged in the horizontal direction, showing the section between the first axial position 60 and the second axial position 61. In this example there are two opposite button in/out splines 52, each represented by an indication of the corresponding set/deliver path 62, and two appertaining cancel splines 53, each represented by an indication of the corresponding cancel path 63. As indicated by the arrows, the set/deliver path 62 can be travelled in both directions, whereas the cancel path 63 can only be travelled from the second axial position 61 to the first axial position 60. In the embodiment represented in FIG. 12, the cancel path 63 starts at the second axial position 61 and ends at the first axial position 60, where the dose member 34 has been rotated 180°.

Figure 13:
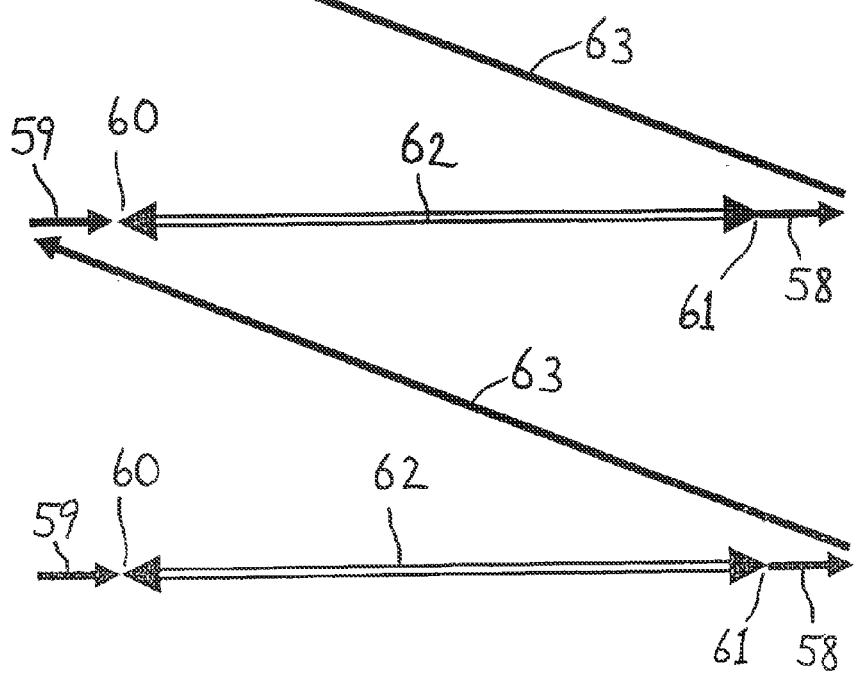
FIG. 13 shows a further example of an arrangement of a set/deliver path and a cancel path in a planar evolution.

FIG. 13 shows a further example according to FIG. 12 but differing by a start path 58 and an end path 59 between the second axial position 61 and the cancel path 63 and between the cancel path 63 and the first axial position 60, respectively. In this embodiment, a cancellation is started by a deliberate pull of the dose member 34 in the proximal direction to move the dose member 34 through the start path 58. This movement may be impeded by a bump feature 55, for instance. After the start path 58 has been travelled, the actual cancel path 63 can be followed to cancel the set dose. At the end of the cancel path 63, a further movement in the proximal direction along the end path 59 resets the dose member 34 to the first axial position 60, from where a further setting can be performed. A bump feature 55' may be provided at the end of the cancel path 63 and/or at the end of the end path 59. In further embodiments only a start path 58 or only an end path 59 may be provided. The start path 58 and/or the end path 59 may be provided to direct the user regarding a deliberate and conscious application of the set/cancel features implemented in the drive mechanism.

Figure 14:
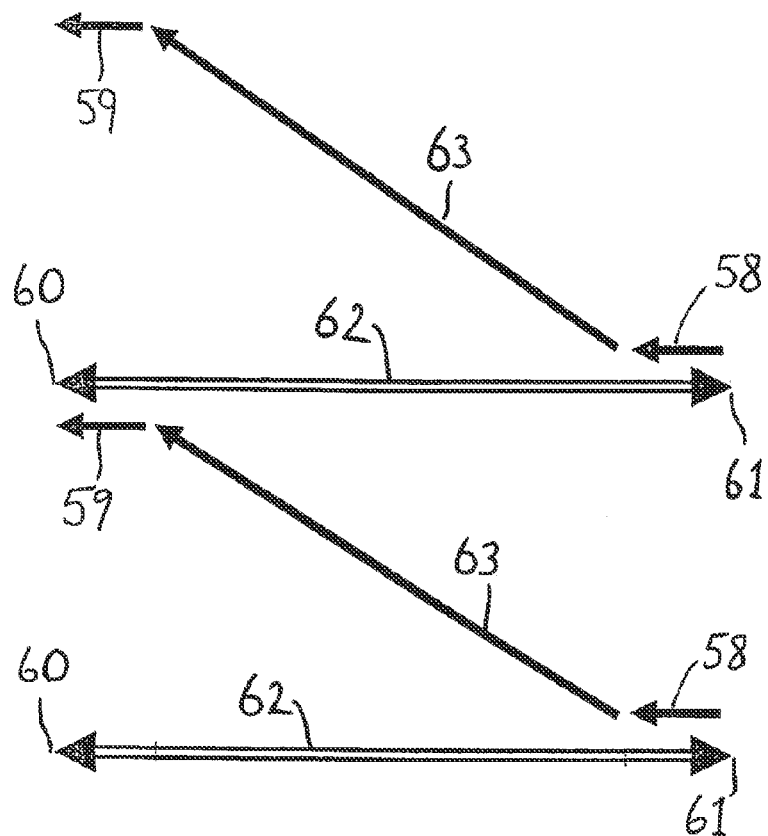
FIG. 14 shows a further example of an arrangement of a set/deliver path and a cancel path in a planar evolution.

FIG. 14 shows a further example according to FIG. 13 but differing in that the start path 58 and the end path 59 are travelled in distal direction. A rotation of the drive member 20 during the movements of the dose member 34 along the start path 58 and the end path 59 may be prevented by a suitable design of the engagement between the dose member 34 and the rotation member 21.

Figure 15:
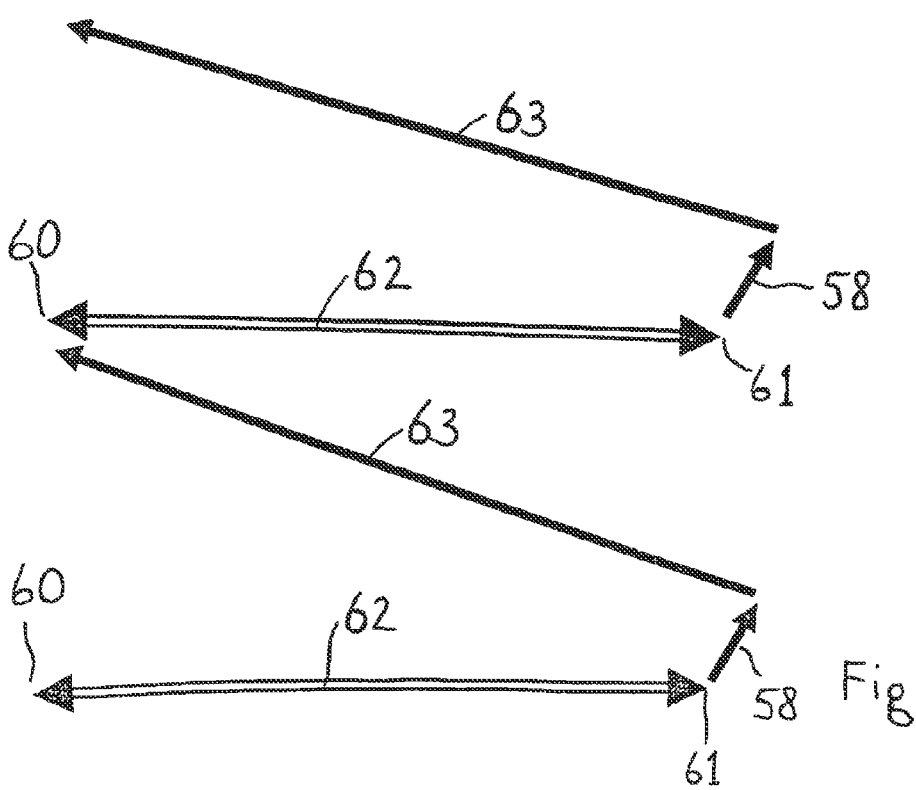
FIG. 15 shows a further example of an arrangement of a set/deliver path and a cancel path in a planar evolution.

FIG. 15 shows a further example of an arrangement of the set/deliver path 62 and the cancel path 63 in a planar evolution. The start path 58 is directed obliquely in proximal direction and requires a rotation of the dose member 34. The direction of the movement of the dose member 34 through the start path 58 is essentially different from the direction of the movement of the dose member 34 through the cancel path 63, so that the start path 58 and the cancel path 63 are distinct, although they both comprise a rotation of the dose member 34. The examples show how different arrangements of set/deliver paths 62 or button in/out splines 52, respectively, and cancel paths 63 or cancel splines 53, respectively, offer a variety of designs, which may be desired by the users, to render the handling of the drive mechanism most comfortable.

Further embodiments may be provided with means to prevent a reversal of the cancellation. This may be achieved by a mechanism that allows a rotation of the dose member 34 in only one direction during the third type of movement between the first axial position and the second axial position. Such a mechanism may be a ratcheting mechanism, for example. An embodiment is shown in the cross-section of FIG. 16. In this embodiment a ratchet insert 66 is arranged between the dose member 34 and the housing or an insert 46 that is fixed to the housing. The ratchet insert 66 is rotatable and preferably axially fixed with respect to the housing 13, 17, and it is rotationally locked with the dose member 34. This may be achieved by guide features 65, 67, which permit an axial movement of the dose member 34 with respect to the ratchet insert 66. The ratchet insert 66 comprises at least one pawl 56, which is coupled to a ratchet 57 on an inner wall of the housing or insert 46. The pawl 56 and the ratchet 57 provide a unidirectional rotational coupling between the dose member 34 and the housing. The insert 46 may be a lock ring used to keep the rotation member 21 in its axial position within the housing. The use of an insert 46 may facilitate the assembling of the mechanism. A possible arrangement of an insert 46 used as a lock ring, the rotation member 21, the dose member 34 and a ratchet insert 66 within a housing part 17 can be seen from FIG. 11.

The pawl 56 may be resilient or resiliently mounted on the ratchet insert 66 in such a manner that the pawl 56 is kept in contact with the ratchet 57 or at a sufficiently small distance from the ratchet 57. The ratchet 57 may be formed by splines having a steep lateral surface, so that the pawl 56 can only slide over the splines in one direction of rotation. Thus, regarding the embodiment and its arrangement shown in the cross-section of FIG. 16, the dose member 34 is only able to rotate clockwise with respect to the insert 46, unless an excessive torque is applied. A rotation of the dose member 34 within its first axial position may be permitted if the ratcheting mechanism and/or the rotational locking between the dose member 34 and the ratchet insert 66 is axially confined. This allows the dose member 34 to be rotated into its initial position after setting and cancellation, which may be required in an embodiment comprising only one button in/out spline 52, for example.

Although the present invention and its advantages have been described in detail, it should be understood that various changes, substitutions and alterations can be made herein without departing from the spirit and scope of the invention as defined by the appended claims.

The invention claimed is:

1. A drive mechanism for a drug delivery device, comprising:
   a housing,
   a piston rod arranged inside the housing,
   a drive member arranged inside the housing, the drive member being rotatable with respect to the housing,
   a rotation member rotatable with respect to the housing,
   a dose member, which is movable between a first axial position with respect to the housing and a second axial position that is axially spaced from the first axial position,
   an engagement of the dose member with the housing, the engagement allowing the dose member to move according to a set/deliver path between the first axial position and the second axial position in either direction or to move according to a cancel path from the second axial position to the first axial position, and
   an engagement of the dose member with the rotation member and a unidirectional rotational engagement of the rotation member with the drive member by a clutch in such a manner that the rotation member is rotated when the dose member is moved according to the set/deliver path and the drive member is not rotated when the dose member is moved according to the cancel path,
   wherein the piston rod comprises a thread engaged with the housing such that a rotational movement of the piston rod is converted into a movement of the piston rod with respect to the housing in a distal direction,
   wherein the piston rod comprises a track engaged with the drive member such that an axial movement of the piston rod relative to the drive member is allowed and a rotational movement of the drive member with respect to the housing is converted into a rotational movement of the piston rod with respect to the housing, and
   wherein the dose member is threadedly engaged with the rotation member.

2. The drive mechanism of claim 1, wherein the cancel path implies a helical movement of the dose member with respect to the housing.

3. The drive mechanism of claim 1, wherein the cancel path implies a helical movement of the dose member with respect to the housing and a subsequent rotation of the dose member within the first axial position.

4. The drive mechanism according to claim 1, wherein the set/deliver path is connected to the cancel path via a start path located between the second axial position and the cancel path and/or via an end path located between the cancel path and the first axial position.

5. The drive mechanism of claim 1, further comprising:
   an engagement member being provided on the rotation member or on the dose member, the dose member being engaged with the rotation member by the engagement member being guided in a thread.

6. The drive mechanism of claim 1, further comprising:
   a button in/out spline and a cancel spline,
   the dose member being engaged with the housing by means of the button in/out spline and the cancel spline,
   the button in/out spline being adapted to guide the movement of the dose member according to the set/deliver path, and
   the cancel spline being adapted to guide the movement of the dose member according to the cancel path.

7. The drive mechanism of claim 6, further comprising:
   at least one bump feature of the cancel spline, the bump feature impeding an entrance into the cancel path or an exit from the cancel path.

8. The drive mechanism of claim 1, further comprising:
   the clutch being formed by an azimuthally arranged series of ramped teeth on the drive member and a corresponding azimuthally arranged further series of ramped teeth on the rotation member.

9. The drive mechanism of claim 1, further comprising:
   a stop member rotationally locked with the housing,
   the stop member being unidirectionally rotationally engaged with the drive member by a further clutch permitting a rotation of the drive member that is generated by a movement of the dose member from the second axial position to the first axial position according to the set/deliver path.

10. The drive mechanism of claim 9, further comprising:
the further clutch being formed by a further azimuthally arranged series of ramped teeth on the drive member and a corresponding azimuthally arranged further series of ramped teeth on the stop member.

11. The drive mechanism of claim 9, further comprising:
a resilient member which exerts a force tending to keep the drive member and the stop member in contact and to keep the drive member and the rotation member in contact.

12. The drive mechanism of claim 1, wherein the set/deliver path is axially directed, and wherein the cancel path is helically wound.

13. The drive mechanism of claim 1, wherein the movement of the dose member from the second axial position to the first axial position according to the set/deliver path generates an axial displacement of the piston rod with respect to the housing by a fixed predetermined distance.

14. The drive mechanism of claim 1, further comprising:
a unidirectional rotational engagement between the dose member or a button that is fixed to the dose member and the housing or an insert that is fixed to the housing.

15. The drive mechanism of claim 14, further comprising:
a ratchet insert comprising at least one pawl, the ratchet insert being rotationally locked with the dose member, and
a ratchet on the housing or insert fixed to the housing, the pawl and the ratchet providing a unidirectional rotational engagement.

16. A drug delivery device comprising a drive mechanism according to claim 1, wherein the drug delivery device is a pen-type injection device.

17. A drive mechanism for a drug delivery device, comprising:
a housing,
a drive member arranged inside the housing, the drive member being rotatable with respect to the housing,
a rotation member rotatable with respect to the housing,
a dose member, which is movable between a first axial position with respect to the housing and a second axial position that is axially spaced from the first axial position,
an engagement of the dose member with the housing, the engagement allowing the dose member to move according to a set/deliver path between the first axial position and the second axial position in either direction or to move according to a cancel path from the second axial position to the first axial position, and
an engagement of the dose member with the rotation member and a unidirectional rotational engagement of the rotation member with the drive member by a clutch in such a manner that the rotation member is rotated when the dose member is moved according to the set/deliver path and the drive member is not rotated when the dose member is moved according to the cancel path,
a stop member rotationally locked with the housing,
the stop member being unidirectionally rotationally engaged with the drive member by a further clutch permitting a rotation of the drive member that is generated by a movement of the dose member from the second axial position to the first axial position according to the set/deliver path, and
wherein the further clutch being formed by a further azimuthally arranged series of ramped teeth on the drive member and a corresponding azimuthally arranged further series of ramped teeth on the stop member.

* * * * *